(12) United States Patent
Luque Vera et al.

(10) Patent No.: US 10,426,858 B2
(45) Date of Patent: Oct. 1, 2019

(54) DEVICE FOR RELEASING VOLATILE SUBSTANCES

(71) Applicant: ZOBELE ESPAÑA, S.A., Barcelona (ES)

(72) Inventors: Sergio Luque Vera, Barcelona (ES); Dominic Doyle, Barcelona (ES); Chao Hsu Lee, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 12 days.

(21) Appl. No.: 15/535,154

(22) PCT Filed: Dec. 10, 2015

(86) PCT No.: PCT/ES2015/070890
§ 371 (c)(1),
(2) Date: Jun. 12, 2017

(87) PCT Pub. No.: WO2016/092137
PCT Pub. Date: Jun. 16, 2016

(65) Prior Publication Data
US 2017/0340766 A1    Nov. 30, 2017

(30) Foreign Application Priority Data

Dec. 12, 2014  (ES) .................................. 201431828

(51) Int. Cl.
*A61L 9/12*    (2006.01)
*B01F 3/04*    (2006.01)
(Continued)

(52) U.S. Cl.
CPC   *A61L 9/12* (2013.01); *A61L 9/04* (2013.01); *A61L 9/14* (2013.01); *A61L 9/16* (2013.01);
(Continued)

(58) Field of Classification Search
CPC ..................................... A61L 9/12; B01F 3/04
(Continued)

(56) References Cited

U.S. PATENT DOCUMENTS

2002/0197188 A1    12/2002 Lua

FOREIGN PATENT DOCUMENTS

CA      2029095       1/1992
GB      2 376 414 A   12/2002
(Continued)

OTHER PUBLICATIONS

International Search Report issued by the International Searching Authority (ISA/O.E.P.M.) dated Mar. 7, 2016 in connection with International Application No. PCT/ES2015/070890.

*Primary Examiner* — Robert A Hopkins
(74) *Attorney, Agent, or Firm* — Gary J. Gershik; Cooper & Dunham LLP

(57) ABSTRACT

The device for releasing volatile substances comprises a support (9) for positioning a receptacle (3) containing the volatile substances, and means for generating a flow of air for releasing the volatile substances, and which is characterized in that said means for generating a flow of air comprise a mobile body (1) joined to said support (9), at least one magnet (2) disposed in said mobile body (1), and means for generating a magnetic flux (4, 5), the operation of which causes the movement of said mobile body (1) by means of the repulsive force between the at least one magnet (2) in the mobile body (1) and the magnetic flux.
An improvement in the energy consumption is permitted, using a low-consumption periodic operation, aided by magnetic means.

10 Claims, 3 Drawing Sheets

(51) Int. Cl.
  *A61L 9/04*   (2006.01)
  *A61L 9/14*   (2006.01)
  *A61L 9/16*   (2006.01)

(52) U.S. Cl.
  CPC ............. *B01F 3/04* (2013.01); *A61L 2209/13* (2013.01); *A61L 2209/15* (2013.01)

(58) Field of Classification Search
  USPC ..................................................... 261/30, 26
  See application file for complete search history.

(56) References Cited

FOREIGN PATENT DOCUMENTS

| | | | | | |
|---|---|---|---|---|---|
| JP | 2006068505 A | * | 3/2006 | ............... | A61L 9/12 |
| WO | WO 2000/35497 | | 6/2000 | | |

* cited by examiner

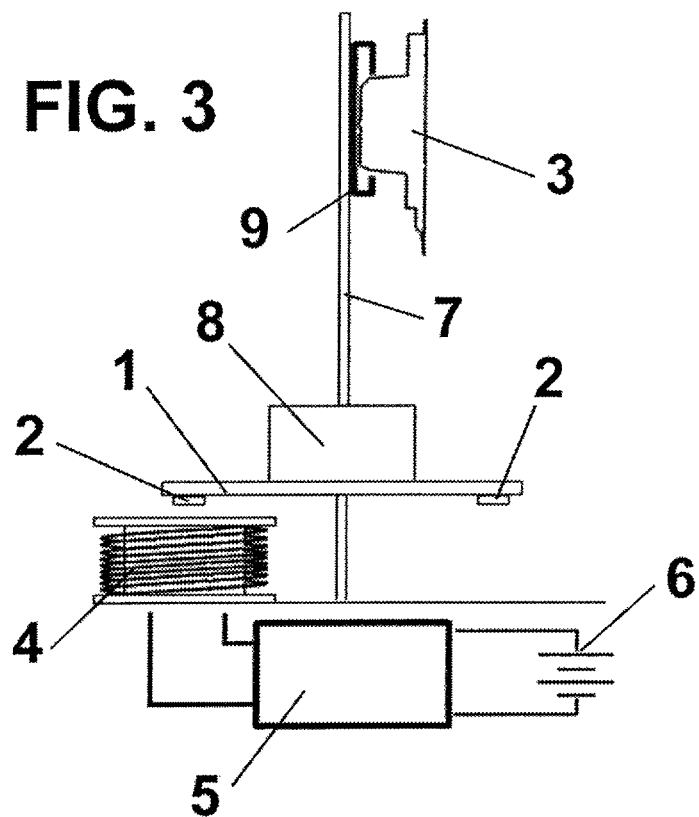
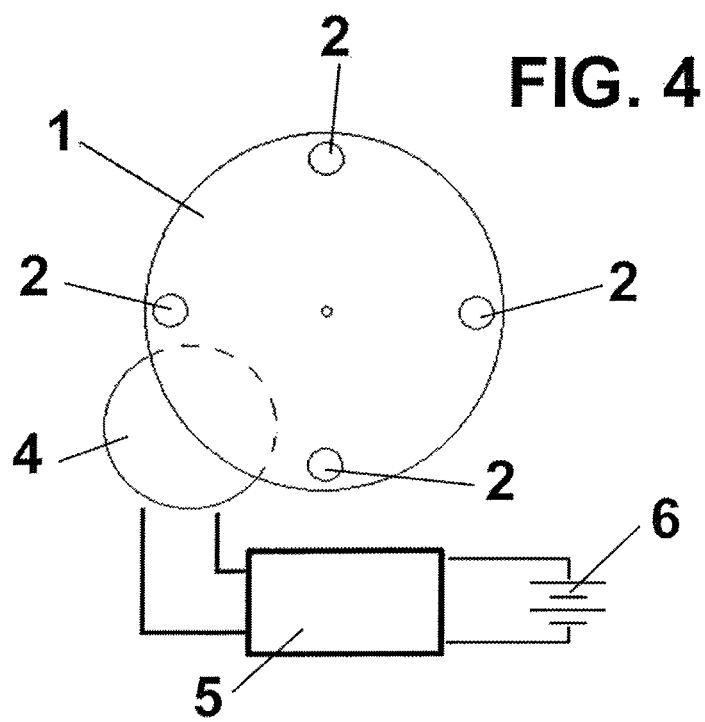

DEVICE FOR RELEASING VOLATILE SUBSTANCES

RELATED APPLICATIONS

This application is a § 371 national stage of PCT International Application No. PCT/ES2014/070884, filed Dec. 1, 2014, claiming priority of Spanish Patent Application P201431828, filed Dec. 12, 2014, the contents of each of which are hereby incorporated by reference into this application The present invention relates to a device for releasing volatile substances that permits generation of a flow of air with an aroma generated by a volatile substance.

BACKGROUND OF THE INVENTION

One currently known type of air freshener or system for releasing volatile substances is formed by a receptacle or container inside of which an air freshening product or a volatile substance, which can be fragrances, pesticides, etc., is housed.

When manufactured, said container is hermetically sealed such that the air freshening product retains all of its aroma in a way that when it is going to be used, removal of the hermetic seal is necessary.

One problem of these currently known air fresheners or systems for releasing volatile substances is that simply opening a receptacle or container may not lead to the desired dispersion of the aroma of said air freshening product.

To solve this problem, systems for releasing volatile substances comprising means for generating a flow of air to correctly disperse the aroma of the air freshening product are already known, for example, fans, heaters, atomizers, nebulizers, aerosols, or passive evaporation elements.

Currently existing solutions have distinct disadvantages, such as excessively high energy consumption in the case of heaters, which generally requires a connection to an electrical grid in order to meet the energy requirements.

In the case of atomizers, nebulizers and fans, energy consumption is more moderate, and it permits the use of batteries; however, the disadvantage is that the batteries must be replaced frequently and on a regular basis. Furthermore, another disadvantage of these types of devices is the difficulty or lack of regulation of the intensity of the release speed.

Another disadvantage of the fans and sprayers is the sound they produce upon releasing the volatile substances, which can be bothersome to the user.

Therefore, a first objective of the present invention is to provide a system for releasing volatile substances that permits the proper release of the volatile substances with the lowest energy expenditure possible.

DESCRIPTION OF THE INVENTION

The device for releasing volatile substances of the invention resolves the aforementioned drawbacks and has other advantages which are described below.

The device for releasing volatile substances according to the present invention comprises a support for positioning a receptacle containing the volatile substances, and means for generating a flow of air for releasing the volatile substances, and which is characterized in that said means for generating a flow of air comprise:
  a mobile body joined to said support;
  at least one magnet disposed in said mobile body; and
  means for generating a magnetic flux, the operation of which causes the movement of said mobile body by means of the repulsive force between the at least one magnet in the mobile body and the magnetic flux.

Furthermore, said means for generating a magnetic flux are disposed close to the mobile body in at least one of the positions of said mobile body, and they comprise a detector that drives the generation of magnetic flux upon detecting the magnet or one of the magnets of said mobile body.

According to an embodiment, said mobile body is a swinging arm with respect to one of its ends, and the magnet is preferably disposed in the swinging arm on the end opposite to the end with respect to the one that swings.

According to another embodiment, said mobile body is a rotary disc with respect to its center, and said rotary disc comprises a plurality of magnets disposed near to its outer portion, said magnets being preferably equidistant to each other.

According to a preferred embodiment, said means for generating a magnetic flux comprise an induction coil, which is powered by one or more batteries.

According to two alternative embodiments, the support for the receptacle containing volatile substances can be positioned in the mobile body, or positioned in a rod joined to the mobile body, preferably in one of the ends of the rod.

In this case, if desired, the end of the rod opposite the receptacle containing volatile substances can comprise a counterweight.

Furthermore, said rotary disc can be connected to a gearbox to advantageously reduce the rotational speed.

The device for releasing volatile substances according to the present invention provides at least the following advantages:
  an improvement in the energy consumption is permitted, using a low-consumption periodic operation, aided by magnetic means. This periodic operation promotes low energy consumption, extending the useful life of the batteries;
  it provides a continuous release of the volatile substances, via the use of membranes, gels, waxes, impregnated solids, etc.;
  an adjustment to the intensity of the release of the volatile substances is permitted by adjusting some variables of movement of the volatile substances container, such as the swinging range, the frequency, the rotational speed, etc.

BRIEF DESCRIPTION OF THE DRAWINGS

For the purpose of helping to make the foregoing description more readily understandable, it is accompanied by a set of drawings which, schematically and by way of illustration and not limitation, represent an embodiment.

FIG. 3 is a side elevation view of the device for releasing volatile substances of the present invention, according to a third embodiment; and FIG. 4 is a plan view of the device for releasing volatile substances of the present invention, according to the third embodiment.

DESCRIPTION OF A PREFERRED EMBODIMENT

Figure 1:
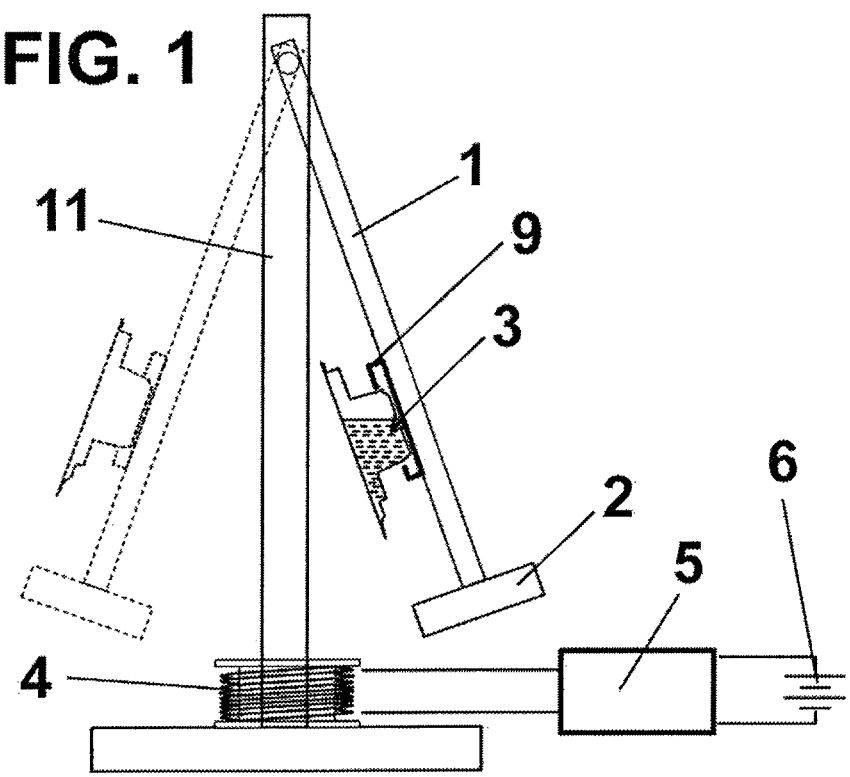
FIG. 1 is a side elevation view of the device for releasing volatile substances of the present invention, according to a first embodiment.

FIG. 1 shows a first embodiment of the device for releasing volatile substances according to the present invention.

According to this embodiment, the volatile substances are contained in a receptacle 3 that is secured to a support 9 mounted on a mobile body 1.

It should be noted that the volatile substances can be aromatic substances to perfume the surroundings or insecticide substances or any other suitable substances, and the receptacle can comprise membranes, gels, waxes, impregnated solids, etc. for correctly releasing the volatile substances.

In a first embodiment, the mobile body 1 is a swinging arm, such as a hanging arm, which comprises a magnet 2 in its lower end (according to the embodiment shown).

Said mobile body 1 is secured in a swinging way to a support structure 11 in its upper end, such that the mobile body 1 will be moved between the positions shown on the continuous line and on the dotted line in FIG. 1.

The device according to the present invention also comprises means for generating magnetic flux comprising an induction coil 4 located around the magnet 2 when the mobile body 1 is located in its vertical position, according to the embodiment shown.

The induction coil 4 is connected to a circuit 5, which functions as a detector to detect the closeness of said magnet 2, and is also connected to one or more batteries 6 in order to power the means for generating magnetic flux.

As can be seen in FIG. 1, the induction coil 4 is located in the lower portion of said support structure 11, and when the mobile body 1 is located in its vertical position, said induction coil 4 is operated by the circuit 5 when the closeness of the magnet 2 is detected, generating magnetic flux that repels the magnet 2, causing the swinging movement of the mobile body 1.

This swinging movement of the mobile body 1 facilitates the release of the volatile substances by generating a flow of air, and the device according to the present invention spends the greatest amount of energy when the induction coil 4 is activated.

Figure 2:
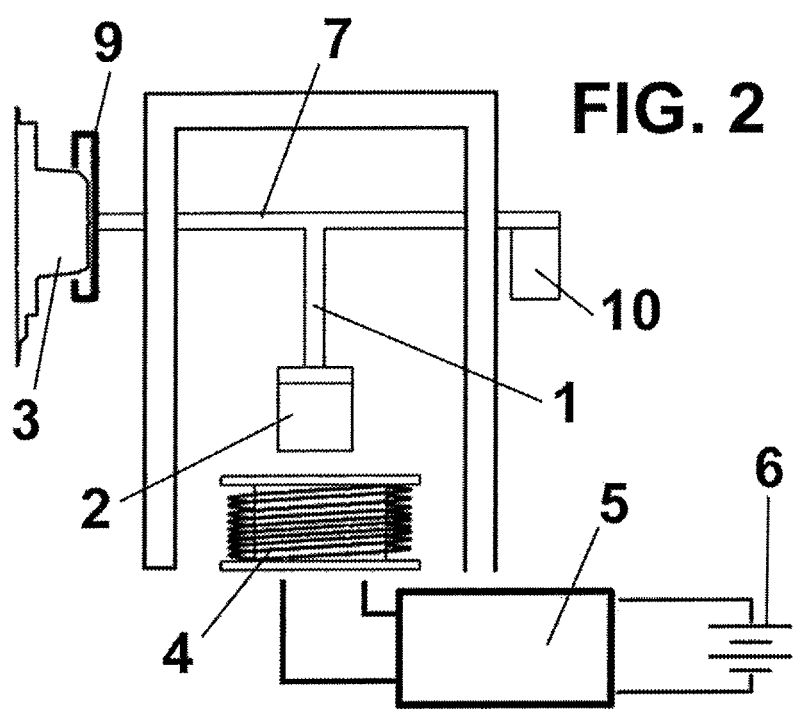
FIG. 2 is a side elevation view of the device for releasing volatile substances of the present invention, according to a second embodiment.

FIG. 2 show a second embodiment of the device according to the present invention.

It should be noted that to provide the description, the same numerical references have also been used to identify the same elements or elements equivalent to the first embodiment.

In this embodiment, the main difference with respect to the previous embodiment is the disposition of the support 9 for the container 3, which in this case is disposed in a rod 7 joined in rotation to the mobile body 1, which, in this embodiment, also has a swinging arm provided with a magnet 2 in its lower end.

In this case, the mobile body 1 is joined on its upper end to said rod 7, preferably in a middle position of the rod 7, and it can comprise a counterweight 10 in its end opposite to the support 9 in order to compensate the weight of the container 3.

In this embodiment, the device according to the present invention also comprises an induction coil 4, a circuit 5 and one or more batteries 6, the operation of which is the same as in the previous embodiment. In this case, however, the container 3 will describe a rotational movement around the longitudinal axis of said rod 7, and not a swinging movement, as in the case of the previous embodiment.

FIGS. 3 and 4 show a third embodiment of the device according to the present invention.

As in the previous case, it should be noted that to provide the description, the same numerical references have been used to identify the same elements or elements equivalent to the first embodiment.

In this embodiment, the main difference with respect to previous embodiments is the mobile body 1, which in this case is a rotary disc with respect to its center, which is provided with a plurality of magnets 2, four in the case of the embodiment shown, placed equidistantly from the outer portion of the disc, and as can be seen in FIG. 3, in its lower portion, near the induction coil 4.

According to this embodiment, the support 9 of the container 3 is disposed in one end of the rod 7, which is joined in rotation to the mobile body 1. In this way, the receptacle 3 will rotationally move around the longitudinal axis of the rod 7.

In this third embodiment, the device according to the present invention can comprise a gearbox 8, positioned between the mobile body 1 and the rod 7. This gearbox can be used to reduce the rotational speed and increase the torque.

In this embodiment, the device according to the present invention also comprises an induction coil 4, a circuit 5 and one or more batteries 6, the operation of which is the same as in the previous embodiments.

These embodiments can be adjusted or improved in the following way:

Energy efficiency can be improved by using a larger induction coil or a stronger magnet, varying the swinging range, adjusting the current, adjusting the equilibrium point, varying the pivot point or varying the total weight of the device.

Despite the fact that reference has been made to a specific embodiment of the invention, it is evident for the person skilled in the art that numerous variations and changes may be made to the device for releasing volatile substances described, and that all the aforementioned details may be substituted by other technically equivalent ones, without detracting from the scope of protection defined by the attached claims.

The invention claimed is:

1. A device for releasing volatile substances comprising:
   a support (9) for positioning a receptacle (3) containing the volatile substances; and
   means for generating a flow of air for releasing the volatile substances, wherein said means for generating a flow of air comprise:
   a mobile body (1) joined to said support (9);
   at least one magnet (2) disposed in said mobile body (1); and
   means for generating a magnetic flux (4, 5) disposed close to the mobile body (1) in at least one position amongst one or more positions of said mobile body (1) and that comprise a detector (5) that drives the generation of magnetic flux upon detecting the magnet (2) or one of the magnets (2) of said mobile body (1), the operation of which causes the movement of said mobile body (1) by means of the repulsive force between said at least one magnet (2) in the mobile body (1) and the magnetic flux,
   wherein said mobile body (1) is a rotary disc with respect to its center.

2. The device for releasing volatile substances according to claim 1, wherein said rotary disc (1) comprises a plurality of magnets (2) disposed near to its outer portion.

3. The device for releasing volatile substances according to claim 2,
wherein said magnets (2) are arranged equidistantly to each other.

4. The device for releasing volatile substances according to claim 1,
wherein said means for generating a magnetic flux further comprise an induction coil.

5. The device for releasing volatile substances according to claim 4,
wherein said induction coil (4) is powered by one or more batteries (6) and controlled by a circuit which functions as the detector (5).

6. The device for releasing volatile substances according to claim 1,
wherein the support (9) for the receptacle (3) containing volatile substances is positioned on the mobile body (1).

7. The device for releasing volatile substances according to claim 1,
wherein the support (9) for the receptacle (3) containing volatile substances is positioned on a rod (7) joined to the mobile body (1).

8. The device for releasing volatile substances according to claim 7, wherein the support (9) for the receptacle (3) containing volatile substances is positioned on one of the ends of the rod (7).

9. The device for releasing volatile substances according to claim 8,
wherein the end of the rod (7) opposite the receptacle (3) containing volatile substances comprises a counterweight (10).

10. The device for releasing volatile substances according to claim 1,
wherein said rotary disc (1) is connected to a gearbox (8).

* * * * *